US009776958B2

(12) United States Patent
Choi et al.

(10) Patent No.: US 9,776,958 B2
(45) Date of Patent: Oct. 3, 2017

(54) SULFONATE-BASED COMPOUND AND METHOD FOR PREPARING SAME

(71) Applicant: LG CHEM, LTD., Seoul (KR)

(72) Inventors: Hyungsam Choi, Daejeon (KR); Joong Jin Han, Daejeon (KR); Chong Kyu Shin, Daejeon (KR); Youngjea Kim, Daejeon (KR); Esder Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/314,005

(22) PCT Filed: Jun. 18, 2015

(86) PCT No.: PCT/KR2015/006187
§ 371 (c)(1),
(2) Date: Nov. 25, 2016

(87) PCT Pub. No.: WO2015/194880
PCT Pub. Date: Dec. 23, 2015

(65) Prior Publication Data
US 2017/0210707 A1    Jul. 27, 2017

(30) Foreign Application Priority Data
Jun. 18, 2014  (KR) .................. 10-2014-0074440

(51) Int. Cl.
*C07C 309/00*  (2006.01)
*C07C 323/19*  (2006.01)
(52) U.S. Cl.
CPC .................. *C07C 323/19* (2013.01)

(58) Field of Classification Search
CPC .................................................. C07C 323/19
See application file for complete search history.

(56) References Cited

U.S. PATENT DOCUMENTS

2014/0065512 A1    3/2014 Kwon et al.

FOREIGN PATENT DOCUMENTS

KR    10-2008-0109225 A    12/2008
KR    10-2013-0062253 A    6/2013

OTHER PUBLICATIONS

STN 1984 (p. 1, Published 1984).*
E. Paillard et al., "Electrochemical investigation of polymer electrolytes based on lithium 2-(phenylsulfanyl)-1,1,2,2-tetrafluoroethansulfonate", Electrochimica Acta, 2007, vol. 53, pp. 1439-1443.
E. Paillard et al., "Polymer electrolytes based on new aryl-containing lithium perfluorosulfonates", Journal of Fluorine Chemistry, 2012, vol. 134, pp. 72-76.
Fabien Toulgoat et al., "An Efficient Preparation of New Sulfonyl Fluorides and Lithium Sulfonates", Journal of Organic Chemistry, 2007, vol. 72, pp. 9046-9052.
International Search Report for PCT/KR2015/006187 (PCT/ISA/210) mailed on Jul. 13, 2015.

* cited by examiner

*Primary Examiner* — Yevegeny Valenrod
*Assistant Examiner* — Blaine G Doletski
(74) *Attorney, Agent, or Firm* — Birch, Stewart, Kolasch & Birch, LLP

(57) ABSTRACT

The present application relates to a sulfonate-based compound and a method for preparing the same.

11 Claims, 1 Drawing Sheet

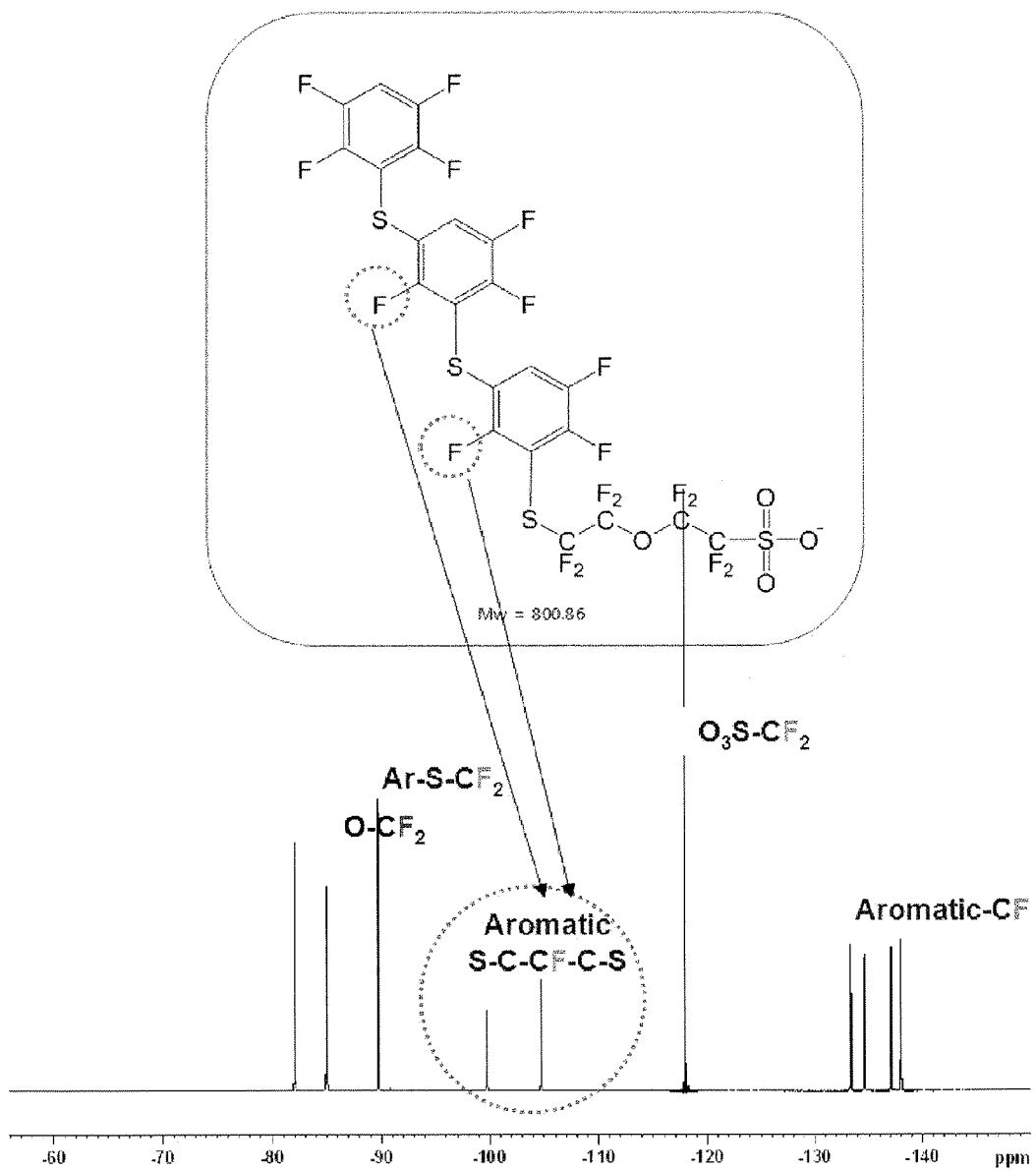

SULFONATE-BASED COMPOUND AND METHOD FOR PREPARING SAME

TECHNICAL FIELD

The present application claims priority to and the benefits of Korean Patent Application No. 10-2014-0074440, filed with the Korean Intellectual Property Office on Jun. 18, 2014, the entire contents of which are incorporated herein by reference.

The present application relates to a sulfonate-based compound and a method for preparing the same.

BACKGROUND ART

Development of various materials has been recently much conducted in diverse technology fields. In addition, development of raw materials used in the development of the various materials has also been conducted therewith. For example, in polymer materials, development of a polymer itself having target properties has been conducted by controlling a polymerization method using known monomers, a combination of monomers in the polymer, a composition ratio or distribution status, a steric structure of the polymer, and side chain length and type. In addition, new monomers used in polymer polymerization have been developed as well.

DISCLOSURE

Technical Problem

The present application provides a sulfonate-based compound and a method for preparing the same.

Technical Solution

In view of the above, one embodiment of the present application provides a compound of the following Chemical Formula 1.

[Chemical Formula 1]

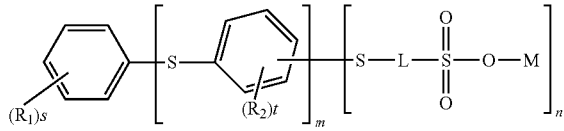

wherein, in Chemical Formula 1, $R_1$ and $R_2$ are the same as or different from each other, and each independently a reactive group or a group convertible to a reactive group, s is an integer of 0 to 5, t is an integer of 3 or 4, m is an integer of 1 to 5, L is a linking group including at least one fluorine atom, n is an integer of 1 or 2, M is a group 1 element of the periodic table, and when s, t, m and n are each an integer of 2 or greater, a plurality of $R_1$s, $R_2$s and substituents in the parentheses is each the same as or different from each other.

Advantageous Effects

Compounds according to one embodiment of the present application are novel, and are highly useful as various materials or raw materials thereof. For example, compounds according to one embodiment of the present application or compounds derived therefrom can be used in preparing polymers.

Compounds according to one embodiment of the present application include a sulfonate group containing a fluorine group, and therefore, polymers having an excellent cation transferring ability can be prepared.

Compounds according to one embodiment of the present application can be prepared to polymers having high cross-linkability and reactivity, and having a high molecular weight.

Compounds according to one embodiment of the present application have a sulfur linking group, and therefore, has excellent acid resistance.

DESCRIPTION OF DRAWINGS

The FIGURE illustrates F-NMR measurement data of a compound according to one embodiment of the present application.

MODE FOR DISCLOSURE

Hereinafter, the present application will be described in detail.

The present application provides a compound of Chemical Formula 1.

In the present specification, a reactive group is a group capable of additionally reacting with other compounds. Specifically, the reactive group means a group capable of reacting with other compounds under reaction conditions known in the art.

In the present specification, a group convertible to a reactive group is a group capable of being additionally substituted with a reactive group, or a group capable of being replaced by a reactive group such as above. Specifically, the group convertible to a reactive group means a group capable of being substituted or replaced by a group capable of reacting with other compounds under reaction conditions known in the art. Types of the group convertible to a reactive group are not particularly limited, and examples thereof may include an alcohol group (hydroxyl group) and the like.

According to one embodiment of the present application, the compound of Chemical Formula 1 has a plurality of reactive groups and groups convertible to a reactive group, and therefore, is highly reactive. Particularly, when forming polymers using the compound of Chemical Formula 1 or monomers derived therefrom, a crosslinking reaction is excellent. Furthermore, polymers having a high molecular weight and excellent solubility may be formed, and the polymers may have excellent proton conductivity due to a sulfonate group containing a fluorine group.

According to one embodiment of the present application, the compound of Chemical Formula 1 has acid resistance by a sulfur (S) linking group, and particularly when forming polymers using the compound of Chemical Formula 1 or compounds derived therefrom, a property of excellent acid resistance may be obtained.

According to one embodiment of the present application, the reactive group is selected from among a halogen group; —OH; —SH; and —NO$_2$.

In the present specification, the halogen group includes F, Cl, Br and I.

According to one embodiment of the present application, the reactive group is a halogen group.

According to one embodiment of the present application, the reactive group is fluorine (F) or chlorine (Cl).

According to one embodiment of the present application, $R_1$ is a halogen group.

According to one embodiment of the present application, $R_2$ is a halogen group.

According to one embodiment of the present application, $R_1$ is fluorine (F) or chlorine (Cl).

According to one embodiment of the present application, $R_2$ is fluorine (F) or chlorine (Cl).

According to one embodiment of the present application, $R_1$ and $R_2$ are the same as or different from each other, and independently a halogen group; —OH; —SH; or —NO$_2$.

According to one embodiment of the present application, when there is a plurality of reactive groups such as a halogen group or groups convertible to a reactive group in the benzene ring in Chemical Formula 1, electron density inside the benzene decreases leading to high reactivity.

According to one embodiment of the present application, m is an integer of 1, 2, 3, 4 or 5, and specifically, m may be 1 or 2.

According to one embodiment of the present application, n may be an integer of 1 or 2.

According to one embodiment of the present application, s is an integer of 0, 1, 2, 3, 4 or 5, and specifically, s may be 4 or 5.

According to one embodiment of the present application, t may be an integer of 3 or 4.

According to one embodiment of the present application, t is 4.

According to one embodiment of the present application, M is hydrogen (H), lithium (Li), sodium (Na) or potassium (K).

When M is lithium (Li), sodium (Na) or potassium (K) in one embodiment of the present application, M forms an ionic bond with $SO_3^-$ lowering the reactivity of $SO_3^-$, and polymerization through only a reactive group in the compound of Chemical Formula 1 according to the present application may be progressed. In this case, M may be ion exchanged to H through a post-treatment process (for example, acid treatment) as necessary.

According to one embodiment of the present application, Chemical Formula 1 is represented by the following Chemical Formula 2.

According to one embodiment of the present application, at least one of R, R', R" and R'" is a fluorine group, and the rest are the same as or different from each other, and each independently hydrogen; a halogen group; or an alkyl group unsubstituted or substituted with a halogen group.

According to one embodiment of the present application, at least one of R, R', R" and R'" is a fluorine group, and the rest are the same as or different from each other, and each independently hydrogen; a halogen group; a methyl group; or a trifluoromethyl (—CF$_3$) group.

According to one embodiment of the present application, at least one of R, R', R" and R'" is a fluorine group, and the rest are a halogen group.

According to one embodiment of the present application, R, R', R" and R'" are fluorine (F).

According to one embodiment of the present application, p is an integer of 0 to 5, q is an integer of 0 to 2, and r is an integer of 1 to 5.

According to one embodiment of the present application, p may be 2.

According to one embodiment of the present application, q may be 1.

According to one embodiment of the present application, r may be 2.

According to one embodiment of the present application, in Chemical Formula 1, L may be —CF$_2$CF$_2$OCF$_2$CF$_2$—.

According to one embodiment of the present application, the compound of Chemical Formula 1 is represented by any one of the following compounds.

[Chemical Formula 2]

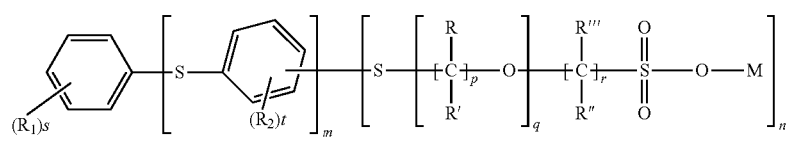

wherein, in Chemical Formula 2, at least one of R, R', R" and R'" is a fluorine group, and the rest are the same as or different from each other, and each independently hydrogen; a halogen group; or an alkyl group unsubstituted or substituted with a halogen group, p is an integer of 0 to 10, q is an integer of 0 to 5, r is an integer of 1 to 10, when p, q and r are each an integer of 2 or greater, substituents in the parentheses are each the same as or different from each other, and $R_1$, $R_2$, s, t, m, n and M are the same as those defined in Chemical Formula 1.

In the present specification, the alkyl group includes a linear or branched having 1 to 60 carbon atoms, and may be further substituted with other substituents. The number of carbon atoms of the alkyl group may be from 1 to 60, specifically from 1 to 40 and more specifically from 1 to 20.

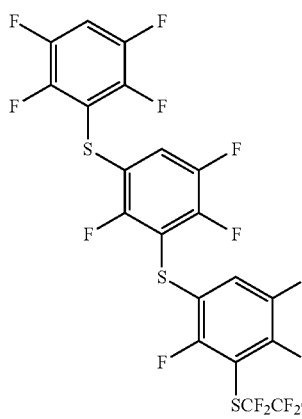

SCF$_2$CF$_2$OCF$_2$CF$_2$SO$_3$K,

-continued

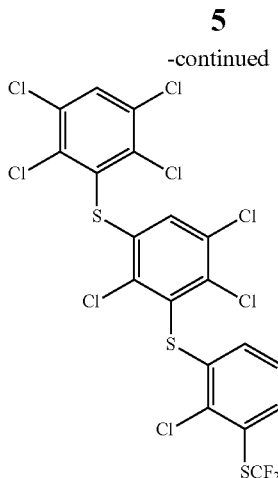

The FIGURE illustrates F-NMR measurement data of a compound having the first structural formula.

Hereinafter, the present application will be described in more detail with reference to examples. However, the following examples are for illustrative purposes only, and the scope of the present application is not limited thereto.

PREPARATION EXAMPLE cl Step 1

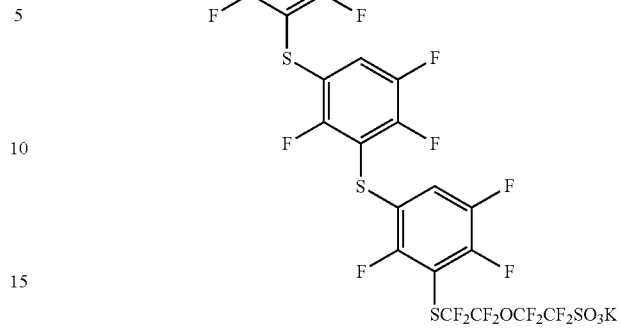

In the step 1, a starting material in which an iodine group and a fluorine group each bond to both ends of a compound including a —$(CF_2)_2$—O—$(CF_2)_2$—group and a —$SO_2$— group was used. First, the starting material was reacted for 4 days at room temperature under the presence of dichloromethane (DCM), $H_2O$, 2,6-lutidine and $Bu_4N^+F^-$ (1 M). Subsequently, tetrahydrofuran (THF) and $K_2CO_3$ were added thereto, and the result was reacted for 10 hours at room temperature to obtain a compound including a —$(CF_2)_2$—O—$(CF_2)_2$— group and a —$SO_3K$— group.

Step 2

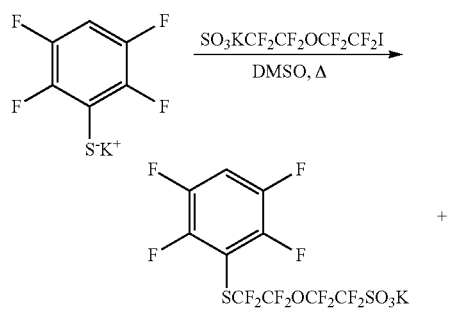

-continued

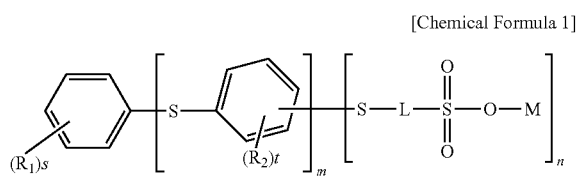

The product obtained in the step 1, a tetrafluorothiophenol salt and DMSO were reacted for 24 hours at 70° C. under nitrogen atmosphere. The result was converted to a compound having 1 benzene ring and a compound having 3 benzene rings in a ratio of approximately 7:3, and the two compounds were separated through recrystallization under aqueous ethanol. As a result, the compound of Chemical Formula 1 according to one embodiment of the present application was obtained.

The invention claimed is:

1. A compound of the following Chemical Formula 1:

[Chemical Formula 1]

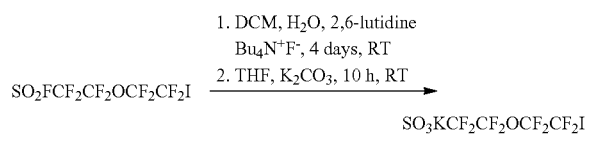

wherein, in Chemical Formula 1, $R_1$ and $R_2$ are the same as or different from each other, and each independently a reactive group or a group convertible to a reactive group;

s is an integer of 0 to 5;

t is an integer of 3 or 4;

m is an integer of 1 to 5;

L is a linking group including at least one fluorine atom;

n is an integer of 1 or 2;

M is a group 1 element of the periodic table; and when s, t, m and n are each an integer of 2 or greater, a plurality of $R_1$s, $R_2$s and substituents in the parentheses is each the same as or different from each other.

2. The compound of claim 1, wherein the reactive group is selected from among a halogen group; —OH; —SH; and —$NO_2$.

3. The compound of claim 1, wherein t is 4.

4. The compound of claim 1, wherein $R_1$ and $R_2$ are the same as or different from each other, and each independently a halogen group; —OH; —SH; or —$NO_2$.

5. The compound of claim 1, wherein $R_1$ is a halogen group.

6. The compound of claim 1, wherein $R_2$ is a halogen group.

7. The compound of claim 1, wherein M is hydrogen (H), lithium (Li), sodium (Na) or potassium (K).

8. The compound of claim 1, wherein Chemical Formula 1 is represented by the following Chemical Formula 2:

[Chemical Formula 2]

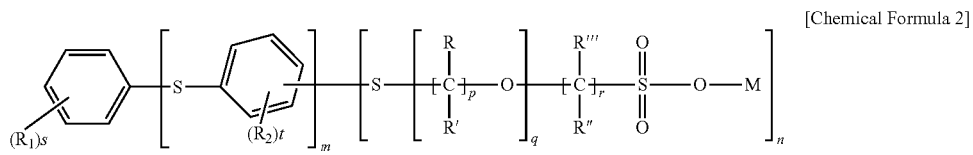

wherein, in Chemical Formula 2, at least one of R, R', R" and R''' is a fluorine group, and the rest are the same as or different from each other, and each independently hydrogen; a halogen group; or an alkyl group unsubstituted or substituted with a halogen group;

p is an integer of 0 to 10;

q is an integer of 0 to 5;

r is an integer of 1 to 10;

when p, q and r are each an integer of 2 or greater, substituents in the parentheses are each the same as or different from each other, and $R_1$, $R_2$, s, t, m, n and M are the same as those defined in Chemical Formula 1.

9. The compound of claim 8, wherein at least one of R, R', R" and R''' is a fluorine group, and the rest are the same as or different from each other, and each independently hydrogen; a halogen group; a methyl group; or a trifluoromethyl (—$CF_3$) group.

10. The compound of claim 8, wherein at least one of R, R', R" and R''' is a fluorine group, and the rest are a halogen group.

11. The compound of claim 8, wherein p is an integer of 0 to 5, q is an integer of 0 to 2 and r is an integer of 1 to 5.

* * * * *